US005683442A

United States Patent [19]

Davidson

[11] Patent Number: 5,683,442
[45] Date of Patent: Nov. 4, 1997

[54] CARDIOVASCULAR IMPLANTS OF ENHANCED BIOCOMPATIBILITY

[75] Inventor: James A. Davidson, Germantown, Tenn.

[73] Assignee: Smith & Nephew, Inc., Memphis, Tenn.

[21] Appl. No.: 745,221

[22] Filed: Nov. 8, 1996

Related U.S. Application Data

[60] Continuation of Ser. No. 468,264, Jun. 6, 1995, abandoned, which is a division of Ser. No. 112,599, Aug. 26, 1993, Pat. No. 5,477,864, which is a continuation-in-part of Ser. No. 36,414, Mar. 24, 1993, Pat. No. 5,509,933, which is a continuation-in-part of Ser. No. 986,280, Dec. 7, 1992, abandoned, which is a continuation-in-part of Ser. No. 647,453, Jan. 28, 1991, Pat. No. 5,169,597, which is a continuation of Ser. No. 454,181, Dec. 21, 1989, abandoned.

[51] Int. Cl.$^6$ ............................................. A61N 1/04
[52] U.S. Cl. ............................................................. 607/116
[58] Field of Search ................................. 607/116, 119, 607/120, 122, 639; 128/642

[56] References Cited

U.S. PATENT DOCUMENTS

| | | |
|---|---|---|
| 2,892,706 | 6/1959 | Jafee et al. . |
| 2,987,352 | 10/1961 | Watson . |
| 3,370,946 | 2/1968 | Bertea et al. . |
| 3,408,604 | 10/1968 | Doi et al. ............................ 335/216 |
| 3,643,658 | 2/1972 | Steinemann . |
| 3,677,795 | 7/1972 | Bokros et al. . |
| 3,752,664 | 8/1973 | Steinemann ............................ 420/417 |
| 3,777,346 | 12/1973 | Steinemann . |
| 3,849,124 | 11/1974 | Villani ............................ 420/417 |
| 3,906,550 | 9/1975 | Rostoker et al. ............................ 3/1.912 |
| 3,911,783 | 10/1975 | Gapp et al. ............................ 420/417 |
| 4,040,129 | 8/1977 | Steinemann et al. ............................ 148/11.5 |
| 4,145,764 | 3/1979 | Suzuki et al. . |
| 4,170,990 | 10/1979 | Baumgart et al. ............................ 606/78 |
| 4,197,643 | 4/1980 | Burstone et al. ............................ 420/421 |
| 4,511,411 | 4/1985 | Brunner et al. . |
| 4,611,604 | 9/1986 | Botuidsson et al. ............................ 607/122 |
| 4,857,269 | 8/1989 | Wang et al. ............................ 420/417 |
| 4,902,359 | 2/1990 | Takeuchi et al. ............................ 148/133 |
| 4,947,866 | 8/1990 | Lessar et al. ............................ 607/116 |
| 4,983,184 | 1/1991 | Steinemann ............................ 623/66 |
| 5,169,597 | 12/1992 | Davidson et al. ............................ 428/613 |

FOREIGN PATENT DOCUMENTS

| | | |
|---|---|---|
| 0 437 079 A1 | 12/1990 | European Pat. Off. . |
| 2703529 | 8/1978 | Germany . |

OTHER PUBLICATIONS

Ferguson, Laing, and Hodge, "The Ionization of Metal Implants in Living Tissues," *JNL of Bone and Joint Surgery*, vol. 42A, No. 1, pp. 77–90 (Jan. 1960).

Hoar and Mears, "Corrosion–Resistant Alloys in Chloride Solutions: Materials for Surgical Implants," pp. 506–507.

Kirk–Othmer Encyclopaedia of Chemical Technology, vol. 23, pp. 98–113.

Jepson, et al., The Science & Tech., Titanium Ed. Jaffee, et al., Pergamon, N.Y., 1968, p. 677.

Heller, et al., Jour. Less Common Metals, 24 (1971) 265.

Van Noort, R., Jour. Mat. Sci., 22 (1987) 3801.

(List continued on next page.)

*Primary Examiner*—William E. Kamm
*Attorney, Agent, or Firm*—Pravel, Hewitt, Kimball & Krieger

[57] ABSTRACT

Medical leads fabricated from low-modulus Ti-Nb-Zr alloys to provide enhanced biocompatibility and hemocompatibility. The medical leads may be surface hardened by oxygen or nitrogen diffusion or by coating with a tightly adherent, hard, wear-resistant, hemocompatible ceramic coating. It is contemplated that the Ti-Nb-Zr alloy can be substituted as a fabrication material for any portion of a medical lead that either comes into contact with blood thereby demanding high levels of hemocompatibility, or that is subject to microfretting, corrosion, or other wear and so that a low modulus metal with a corrosion-resistant, hardened surface would be desirable.

26 Claims, 2 Drawing Sheets

OTHER PUBLICATIONS

The Japan Medical Review, vol. 12, (undated) unnumbered page, pp. 12,23.

Author unknown, "Titanium–Niobium Base Quaternary Alloys," (Date Unknown), pp. 405–419.

Zwicker, et al., Z. Metallkunde, 61 (1970) pp. 836–847.

Collings, E.W., "The Physical Metallurgy of Titanium Alloys," *American Society for Metals*, pp. 40–41, 66–69, 72–73, 120–121, 190–191, 194–195, 214–215, 218–219, 226–227 (no date).

Albert, et al., Z. Metallunde, 62 (1972) 126.

Brown & Merritt, "Evaluation of Corrosion Resistance of Biology," Case Western Reserve University, Feb. 13, 1986 (1:8).

Mears, "Electron–Probe Microanalysis of Tissue and Cells from Implant Areas," *JNL of Bone and Joint Surgery*, vol. 48B, No. 3, pp. 576–76 (Aug. 1966).

CARDIOVASCULAR IMPLANTS OF ENHANCED BIOCOMPATIBILITY

RELATED APPLICATIONS

This application is a continuation of application Ser. No. 08/468,264 filed Jun. 6, 1995, now abandoned, which is a divisional of Ser. No. 08/112,599 filed on Aug. 26, 1993, issued as U.S. Pat. No. 5,477,864, which is a continuation-in-part of application Ser. No. 08/036,414, filed Mar. 24, 1993, issued as U.S. Pat. No. 5,509,933, which is in turn a continuation-in-part of application Ser. No. 07/986,280, filed on Dec. 7, 1992, abandoned, which is a continuation-in-part of application Ser. No. 07/647,453, filed on Jan. 28, 1991, issued as U.S. Pat. No. 5,169,597, which is in turn a continuation of U.S. Ser. No. 07/454,181, filed on Dec. 21, 1989, abandoned.

BACKGROUND OF THE INVENTION

1. Field of the Invention

This invention relates to a range of cardiovascular and other implants fabricated of metallic alloys of enhanced hemocompatibility that can optionally be surface hardened to provide resistance to wear, or cold-worked or cold-drawn to reduce elastic modulus, if necessary. More specifically, the invention is of pacemaker leads and other electrical leads and sensors fabricated of Ti-Nb-Zr alloys.

2. Description of the Related Art

Cardiovascular implants have unique blood biocompatibility requirements to ensure that the device is not rejected (as in the case of natural tissue materials for heart valves and grafts for heart transplants) or that adverse thrombogenic (clotting) or hemodynamic (blood flow) responses are avoided.

Cardiovascular implants, such as heart valves, can be fabricated from natural tissue. These bioprostheses can be affected by gradual calcification leading to the eventual stiffening and tearing of the implant.

Non-bioprosthetic implants are fabricated from materials such as pyrolytic carbon-coated graphite, pyrolytic carbon-coated titanium, stainless steel, cobalt-chrome alloys, cobalt-nickel alloys, alumina coated with polypropylene and poly-4-fluoroethylene.

For synthetic mechanical cardiovascular devices, properties such as the surface finish, flow characteristics, surface structure, charge, wear, and mechanical integrity all play a role in the ultimate success of the device. Pacers, defibrillators, leads, and other similar cardiovascular implants are made of Ni-Co-Cr alloy, Co-Cr-Mo alloy, titanium, and Ti-6Al-4V alloy, stainless steel, and various biocompatible polymers.

One of the most significant problems encountered in heart valves, artificial hearts, assist devices, pacers, leads, stents, and other cardiovascular implants is the formation of blood clots (thrombogenesis). Protein coatings are sometimes employed to reduce the risk of blood clot formation. Heparin is also used as an anti-thrombogenic coating.

It has been found that stagnant flow regions in the devices or non-optimal materials contribute to the formation of blood clots. These stagnant regions can be minimized by optimizing surface smoothness and minimizing abrupt changes in the size of the cross section through which the blood flows or minimizing either flow interference aspects. While materials selection for synthetic heart valves, and cardiovascular implants generally, is therefore dictated by a requirement for blood compatibility to avoid the formation of blood clots (thrombus), cardiovascular implants must also be designed to optimize blood flow and wear resistance.

Even beyond the limitations on materials imposed by the requirements of blood biocompatibility and limitations to designs imposed by the need to optimize blood flow, there is a need for durable designs since it is highly desirable to avoid the risk of a second surgical procedure to implant cardiovascular devices. Further, a catastrophic failure of an implanted device will almost certainly result in the death of the patient.

SUMMARY OF THE INVENTION

The invention provides cardiovascular and other medical implants of a low modulus, biocompatible, hemocompatible, metallic alloy of titanium with niobium and optionally zirconium. The invention implants include pacers, electrical leads and sensors. The invention also provides surface hardened versions of these devices produced by oxygen or nitrogen diffusion hardening to improve resistance to cavitation, microfretting wear, and impact-induced wear.

The inherently low modulus of Ti-Nb-Zr alloys, between about 6 to about 12 million psi depending on metallurgical treatment and composition, provide a more flexible and forgiving construct for cardiovascular applications while improving contact stress levels.

The preferred low modulus titanium alloys of the invention have the compositions: (i) titanium; about 10 wt. % to about 20 wt. % niobium; and optionally from about 0 wt. % to about 20 wt. % zirconium; and (ii) titanium; about 35 wt. % to about 50 wt. % niobium; and optionally from about 0 wt. % to about 20 wt. % zirconium. Tantalum can also be present as a substitute for Nb. These alloys are referred to herein as "Ti-Nb-Zr alloys," even though tantalum may also be present and the zirconium percentage may be zero.

The exclusion of elements besides titanium, zirconium, and niobium, or tantalum results in an alloy which does not contain known toxins or carcinogens, or elements that are known or suspected of inducing diseases or adverse tissue response in the long term.

Without the presence of zirconium in the composition, the ability of the Ti-Nb-Zr alloy to surface harden during oxygen or nitrogen diffusion hardening treatments is more limited. Therefore, presence of zirconium is especially preferred when the alloy implant must be diffusion hardened. Other non-toxic filler materials such as tantalum, which stabilize the β-phase of titanium alloy, but do not affect the low modulus, i.e., maintain it at less than about 85 GPa, could also be added.

BRIEF DESCRIPTION OF THE DRAWINGS

A better understanding of the present invention can be obtained when the following detailed description of the preferred embodiments is considered in conjunction with the following drawings, in which.

DETAILED DESCRIPTION OF THE PREFERRED EMBODIMENTS

Figure 2:
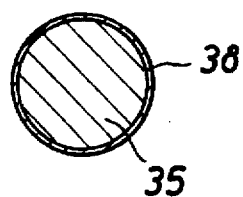
FIG. 2 is a cross section of the lead wire of FIG. 1.

The implants of the invention are fabricated from an alloy containing titanium as a component. The preferred low modulus titanium alloys have the compositions: (i) titanium, about 10 wt. % to about 20 wt. % niobium, and optionally from about 0 wt. % to about 20 wt. % zirconium; and (ii) titanium, about 35 wt. % to about 50 wt. % niobium, and optionally from about 0 wt. % to about 20 wt. % zirconium.

In a preferred embodiment wherein the implants are surface hardened by oxygen or nitrogen diffusion, zirconium is beneficially present in amounts ranging from about 0.5 to about 20 wt. %.

Even though it is apparent that the titanium proportion of alloy used to make the invention implants could be less than 50 wt. % and the zirconium proportion zero percent, nevertheless, for the purposes of this specification, it is referred to as a "Ti-Nb-Zr alloy" or a "titanium alloy." The alloy most preferably comprises about 13 wt. % of zirconium, 13 wt. % of niobium and remainder being titanium. While tantalum may be substituted for niobium to stabilize β-phase titanium, niobium is the preferred component due to its effect of lowering the elastic modulus of the alloy when present in certain specific proportions. Other elements are not deliberately added to the alloy but may be present in such quantities that occur as impurities in the commercially pure titanium, zirconium, niobium, or tantalum used to prepare the alloy and such contaminants as may arise from the alloying process.

In the specification and claims, the term "high strength" refers to an alloy having a tensile strength above at least about 620 MPa.

The term "low modulus," as used in the specification and claims, refers to a Young's modulus below about 90 GPa.

Although the hot rolled, reheated, and quenched Ti-Nb-Zr alloy is a suitable implant material, its properties can be improved by forging or other metallurgical processes or an aging heat treatment or a combination of these. Aging treatment can increase the strength and hardness of the material, and reduce its elongation while maintaining a relatively low modulus of elasticity. The treatment can be varied to obtain the desired properties. U.S. Pat. No. 5,169,597 to Davidson, et al. and U.S. Pat. No. 5,477,864 to Davidson, both hereby fully incorporated by reference, deal in more detail with the useful Ti-Nb-Zr alloys. Further, U.S. Ser. No. 08/036,414, issued as U.S. Pat. No. 5,509,933, hereby fully incorporated by reference, teaches how to hot work Ti-Nb-Zr alloys to produce high strength, low modulus medical implants.

It may be desirable for other reasons, such as reducing microfretting wear between mating mechanical components, to surface harden the alloy implants using oxygen or nitrogen diffusion hardening methods, or coating with a hard wear resistant coating. In the latter event, the surface of the prosthesis may be coated with an amorphous diamond-like carbon coating or ceramic-like coating such as zirconium or titanium oxide, zirconium or titanium nitride, or zirconium or titanium carbide using chemical or plasma vapor deposition techniques to provide a hard, impervious, smooth surface coating. These coatings are especially useful if the prosthesis is subjected to conditions of wear or as an electrically insulative coating on electrical leads (i.e., pacemaker, defibrillator, neurological, sensors) of Ti-Nb-Zr alloy.

Methods for providing hard, low-friction, impervious, biocompatible amorphous diamond-like carbon coatings are known in the art and are disclosed in, for example, EPO patent application 302 717 A1 to Ion Tech and Chemical Abstract 43655P, Vol. 101, describing Japan Kokai 59/851 to Sumitomo Electric, all of which are incorporated by reference herein as though full set forth.

A preferred process for oxygen diffusion hardening is described in the U.S. Pat. No. 5,372,560, which is hereby fully incorporated by reference. Oxygen diffusion hardening according to this process requires the supply of oxygen, or an oxygen containing atmosphere, or compounds partially composed of oxygen, such as water (steam), carbon dioxide, nitrogen dioxide, sulfur dioxide, and the like. These substances are supplied to the implant to be hardened which is maintained at a temperature preferably between 200° C. and 1200° C. The amount of time required at a given temperature to effectively produce the surface and near-surface hardened implants is related exponentially, by an Arhennius-type relationship to the temperature. That is, shorter periods of time are required at higher temperatures for effective diffusion hardening. The resultant oxygen diffusion hardened implants are characterized in that the oxide film contains primarily a mixture of titanium and zirconium oxides in the implant surface. Niobium oxides may also be present. Immediately underlying this mixed-oxide film is sometimes a region of oxygen-rich metal alloy. Underlying the sometimes-obtained oxygen-rich alloy layer is the core Ti-Nb-Zr alloy. The interface between the sometimes-obtained oxygen-rich alloy layer and the oxide regions is typically zirconium-rich in comparison to the underlying Ti-Nb-Zr alloy. In a most preferred embodiment, the Ti-Nb-Zr alloy is subjected to temperature and an environment of argon gas that has been moisturized by bubbling through a water bath. The water vapor disassociates at the implant surface to produce oxygen which diffuses into the implant to produce the desired hardened surface.

Nitrogen diffusion processes can also be utilized in which nitrogen sources are provided instead of oxygen. These nitrogen diffusion surface hardening processes will tend to harden the metal alloy substrate in a similar manner to that of oxygen diffusion hardening or conventional oxygen hardening (which is also useful), and produce a yellow-orange insulative, wear-resistant surface oxide instead of the blue-black surface oxide which typically forms from the in situ oxygen diffusion hardening process.

Further, the implants of the invention may optionally be surface coated with medicaments such as anti-inflammatory agents, anti-thrombus agents, antibiotics, proteins that reduce platelet adhesion, and the like to improve their acceptability in a living body.

Pacemakers and Electrical Signal Carrying Leads/Sensors

Pacemaker and other electronic leads are manufactured by several corporations, including Medtronic, which produces a range of pacemaker lead designs.

Figure 3A:
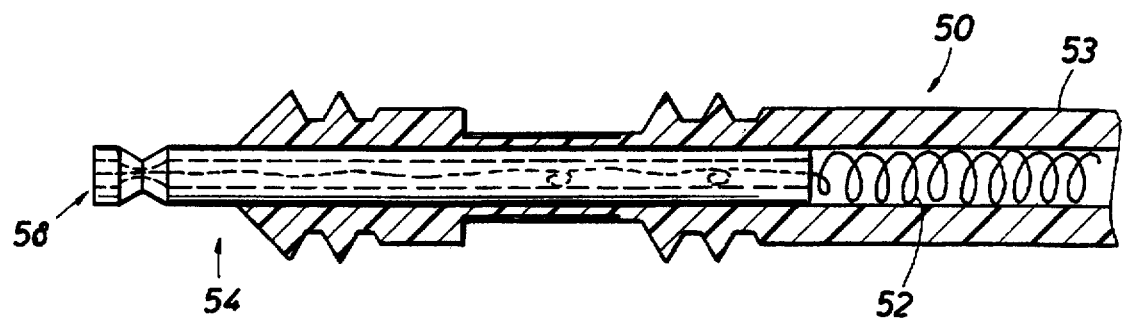
FIGS. 3A-C are schematic diagrams of prior art pacemaker leads with polyurethane covering.
Figure 3B:
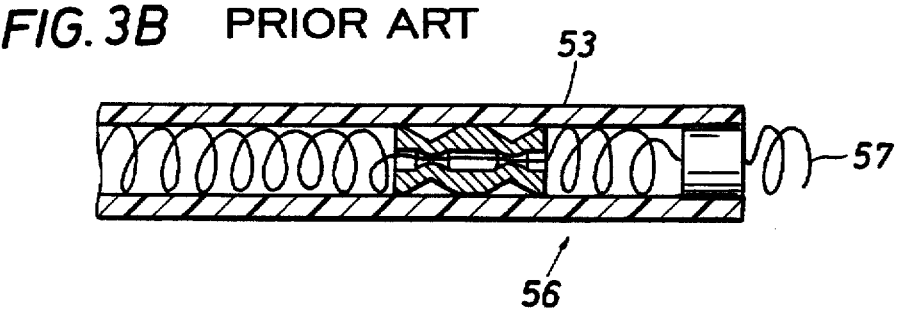
Figure 3C:
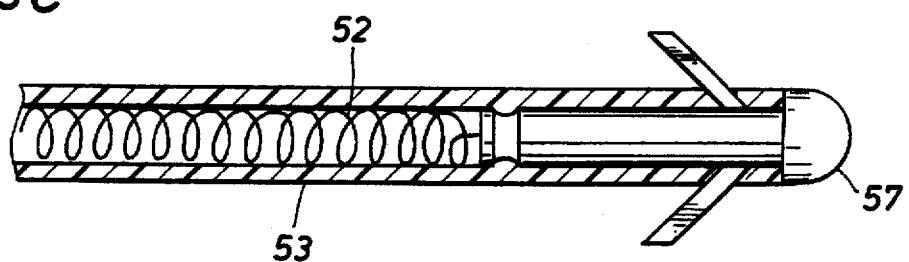
Figure 3D:
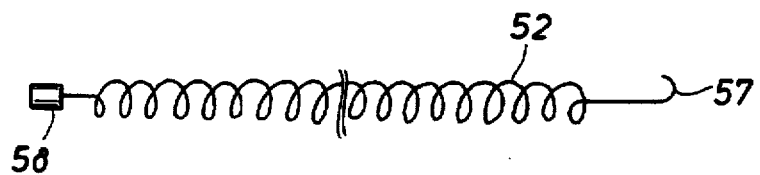
FIG. 3D is a schematic of an embodiment of the invention Ti-Nb-Zr pacemaker leads.

One of these designs is shown in schematic form in FIGS. 3A and B. The pacemaker lead body 150 has a centrally disposed metallic conductor 152 typically made of cobalt-nickel alloy, such as MP35N®. This conductor 152 is usually made up of several strands of wire, each having a diameter of about 0.15–0.20 mm. The conductor 152 is covered by an insulative, protective polymer sheath 153 so that the elongate body 150 of the pacemaker lead has an overall diameter ranging from about 2.2 to about 3 mm. The pacemaker has a first end 154 with an electrode 158 for connecting to a pulse generator and a second end 156 with an electrode 157 for contacting heart muscle. An alternative embodiment is shown in FIG. 3C. As supplied, these two ends are covered with protective polyurethane caps which can be removed for installation of the pacemaker. In order to prevent electrical interference with the conductor 152, a polymeric insulative sleeve 153 is disposed over the entire pacemaker lead body 150, with the exception of the exposed electrodes 157 for contacting heart muscle and the contact electrode 158 for engaging with the pulse generator that houses the electronics and power pack for the pacemaker. As explained before, the organic polymeric sheath compositions, typically polyurethane, can slowly degenerate in the body causing problems, not only due to potential deterioration of electrical insulation and interference with electrical signals but also because of potentially toxic products of degradation.

The invention provides, as shown in FIG. 3C, a pacemaker wherein the conductor 152 is fabricated from a Ti-Nb-Zr alloy that is coated with a tightly adherent, low friction, bio- and hemocompatible coating, with the exception of the electrode for contacting heart muscle 157, and the electrode 158 at the other end of the lead for engaging the pulse generator. The coatings can be formed by in situ oxidation or nitriding of the Ti-Nb-Zr to produce an electrically insulative surface layer of from about 0.1 to about 3 microns in thickness, preferably less than about 0.5 microns in thickness. This process can be carried out at the same time the material is age-hardened. Alternatively, an insulative inert ceramic coating can be applied by conventional CVD or PVD methods either on the original Ti-Nb-Zr alloy surface or onto the diffusion hardened Ti-Nb-Zr surface. For these overlay coatings, the thickness can be as great as 20 microns. The overlay coatings include ceramic metal oxides, metal nitrides, metal carbides, amorphous diamond-like carbon, as detailed above. The electrical signal conductor 152 can comprise either a single wire or multiple wires. Exposed Ti-Nb-Zr metallic ends of the wire or wires are preferably connected directly to a pulse generator thereby avoiding the necessity for a weld or crimp to attach an electrode to the conductor which may result in local galvanic corrosion or physically weakened regions. Further, since the coatings provide a natural protective insulative surface, the use of a coiled construct could be avoided by using only a preferred single-strand, non-coiled low modulus Ti-Nb-Zr metallic wire construct for the conductor 152. This will also eliminate the need for stiff guide wire. Finally, the overall diameter of the pacemaker lead body 150 could be reduced considerably from the range of about 2.2–3 mm for current commercially available leads to about 0.2–1 mm. Optionally, the leads of the invention may be covered with a polymeric sheath.

Defibrillators

Figure 1:
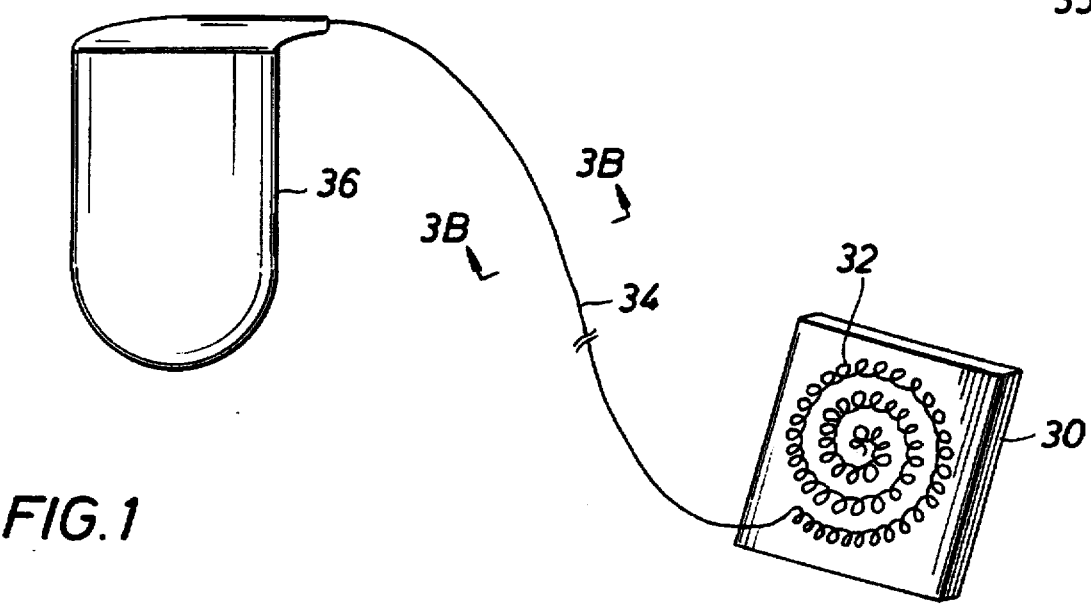
FIG. 1 is a schematic diagram of the components of a defibrillator, showing power source, lead wire, and polymeric patch with coiled electrode.

FIGS. 1 and 2 show a defibrillator including a flexible silicone polymeric patch 300 with a coil of conductive wire 320 (typically titanium, stainless steel, or cobalt-nickel-chromium) on the side of the silicone patch 300 that will contact muscle tissue. When in place in the body, the lead wire 320 that carries power to the coil 340 extends out of the body (through the skin) and is electrically connected to a power source contained in a protective container 360. According to the invention, the lead wire 320 is fabricated with an electrically conductive core 350 of Ti-Nb-Zr alloy and is coated with an adherent electrically insulative coating 380, such as metal oxides, carbides, or nitrides, or with amorphous diamond-like carbon as shown in exaggerated detail FIG. 2. This coating electrically insulates the lead wire from electrical contact with surrounding body tissue while also protecting the metallic core from corrosion and attack by body fluids, as described previously for the pacemaker lead. Elimination of the polymer coating results in the elimination of potentially toxic products of gradual degradation of the polymer and also the consequent shorting the system when the insulative coating is breached.

The Hardened Surfaces

The oxygen or nitrogen diffusion hardened surface of the alloy implants may be highly polished to a mirror finish to further improve blood flow characteristics. Further, the oxide- or nitride-coated surfaces maybe coated with substances that enhance biocompatibility and performance. For example, a coating of phosphatidyl choline, heparin, or other proteins to reduce platelet adhesion to the surfaces of the implant, or the use of antibiotic coatings to minimize the potential for infection. Boronated or silver-doped hardened surface layers on the implant reduces friction and wear between contacting parts of the invention cardiovascular implants. Additionally, amorphous diamond-like carbon, pyrolytic carbon, or other hard ceramic surface layers can also be coated onto the diffusion hardened surface to optimize other friction and wear aspects. The preferred diffusion hardened surface layer described in this application provides a hard, well-attached layer to which these additional hard coatings can be applied with a closer match between substrate and coating with respect to hardness. Other, conventional methods of oxygen surface hardening are also useful. Nitriding of the substrate leads to a hardened nitride surface layer. Methods of nitridation known in the art may be used to achieve a hard nitride layer.

Regardless of how a Ti-Nb-Zr alloy implant's surface is hardened, the friction and wear (tribological) aspects of the surface can be further improved by employing the use of silver doping or boronation techniques. Ion-beam-assisted deposition of silver films onto ceramic surfaces can improve tribiological behavior. The deposition of up to about 3 microns thick silver films can be performed at room temperature in a vacuum chamber equipped with an electron-beam hard silver evaporation source. A mixture of argon and oxygen gas is fed through the ion source to create an ion flux. One set of acceptable silver deposition parameters consists of an acceleration voltage of 1 kev with an ion current density of 25 microamps per $cm^2$. The silver film can be completely deposited by this ion bombardment or formed partially via bombardment while the remaining thickness is achieved by vacuum evaporation. Ion bombardment improves the attachment of the silver film to the Ti-Nb-Zr alloy substrate. Similar deposition of silver films on existing metal cardiovascular implants may also be performed to improve tribological behavior, as well as antibacterial response.

An alternate method to further improve the tribological behavior of Ti-Nb-Zr alloy surfaces of cardiovascular implants is to apply boronation treatments to these surfaces such as commercial available boride vapor deposition, boron ion implantation or sputter deposition using standard ion implantation and evaporation methods, or form a boron-type coating spontaneously in air. Boric Acid ($H_3BO_3$) surface films provide a self-replenishing solid lubricant which can further reduce the friction and wear of the ceramic substrate. These films form from the reaction of the $B_2O_3$ surface (deposited by various conventional methods) on the metal surface with water in the body to form lubricous boric acid. Conventional methods that can be used to deposit either a boron (B), $H_3BO_3$, or $B_2O_3$ surface layer on the cardiovascular implant surface include vacuum evaporation with or without ion bombardment) or simple oven curing of a thin layer over the implant surface. The self-lubricating mechanism of $H_3BO_3$ is governed by its unique layered, triclinic crystal structure which allows sheets of atoms to easily slide over each other during articulation, thus minimizing substrate wear and friction.

Additionally, surfaces (metal or coated) of all the cardiovascular and medical implants discussed may optionally be coated with agents to further improve biological response. These agents include anticoagulants, proteins, antimicrobial agents, antibiotics, and the like medicaments.

Although the invention has been described with reference to its preferred embodiments, those of ordinary skill in the art may, upon reading this disclosure, appreciate changes and modifications which may be made and which do not depart from the scope and spirit of the invention as described above and claimed below.

I claim:

1. A biocompatible lead for conducting electrical signals to or from an organ in a living body, the lead having enhanced hemocompatibility, comprising:
   an elongate flexible body having distal and proximal ends and an electrically conductive core for conducting electrical signals, the core at least partially fabricated from a biocompatible and hemocompatible metal alloy, the alloy comprising:
   (i) titanium; and
   (ii) niobium selected from a non-continuous range of about 10 to about 20 wt. % niobium and from about 35 to about 50 wt % niobium.

2. The lead of claim 1, further having an electrically insulative layer surrounding the electrically conductive core.

3. The lead of claim 2, wherein the electrically insulative layer comprises material selected from the group of electrically insulative materials consisting of metal oxides, metal nitrides and metal carbides.

4. The lead of claim 1, wherein at least a portion of the titanium is β-phase titanium and said alloy further comprises an amount of zirconium sufficient to retard the transformation of β-phase titanium.

5. The lead of claim 4, wherein the metal alloy comprises about 13 wt. % niobium, about 13 wt. % zirconium and the remainder titanium.

6. The lead of claim 4, wherein the amount of zirconium sufficient to retard the transformation of β-phase titanium is less than about 20 wt. % zirconium.

7. The lead of claim 4, wherein the metal alloy comprises from about 0.5 to about 20 wt. % zirconium.

8. The lead of claim 4, further having an electrically insulative layer surrounding the electrically conductive core.

9. The lead of claim 8, wherein the electrically insulative layer comprises material selected from the group of electrically insulative materials consisting of metal oxides, metal nitrides and metal carbides.

10. The lead of claim 1 or claim 4, wherein the core is a single non-coiled wire of said alloy.

11. The lead of claim 1 or claim 4, wherein the core is multiple wires of said alloy.

12. The lead of claim 1, or claim 2 or claim 4, wherein surfaces of the lead that come into contact with body tissue or fluid are at least partially coated with a composition selected from the group consisting of anticoagulants, antimicrobial agents, antibiotics, and medicaments.

13. The lead of claim 1, or claim 2 or claim 4, further comprising a low friction wear-resistant boron-containing outer surface layer on at least a portion of the lead.

14. The lead of claim 1, or claim 2 or claim 4, further comprising a low friction wear-resistant silver-containing outer surface layer on at least a portion of the lead.

15. A biocompatible lead for conducting electrical signals to or from an organ in a living body, the lead having enhanced hemocompatibility, comprising:
   an elongate flexible body having distal and proximal ends and an electrically conductive core for conducting electrical signals, the core at least partially fabricated from a biocompatible and hemocompatible metal alloy, the alloy comprising:
   (i) titanium; and
   (ii) niobium and tantalum, with a combined wt. % of niobium and tantalum selected from a non-continuous range of about 10 to about 20 wt. % and from about 35 to about 50 wt. %.

16. The lead of claim 15, further having an electrically insulative layer surrounding the electrically conductive core.

17. The lead of claim 16, wherein the electrically insulative layer comprises material selected from the group of electrically insulative materials consisting of metal oxides, metal nitrides and metal carbides.

18. The lead of claim 15, wherein at least a portion of the titanium is β-phase titanium and said alloy further comprises an amount of zirconium sufficient to retard the transformation of β-phase titanium.

19. The lead of claim 18, wherein the metal alloy comprises from about 0.5 to about 20 wt. % zirconium.

20. The lead of claim 18, further comprising an electrically insulative layer surrounding the electrically conductive core.

21. The lead of claim 20, wherein the electrically insulative layer comprises material selected from the group of electrically insulative materials consisting of metal oxides, metal nitrides and metal carbides.

22. The lead of claim 15 or claim 20, wherein the core is a single non-coiled wire of said alloy.

23. The lead of claim 15 or claim 20, wherein the core is multiple wires of said alloy.

24. The lead of claim 15, or claim 16 or claim 18, further having lead surfaces that come into contact with body tissue or fluid, said surfaces at least partially coated with a composition selected from the group consisting of anticoagulants, antimicrobial agents, antibiotics, and medicaments.

25. The lead of claim 15, or claim 16 or claim 18, further comprising a low friction wear-resistant boron-containing outer surface layer on at least a portion of the lead.

26. The lead of claim 15, or claim 16 or claim 18, further comprising a low friction wear-resistant silver-containing outer surface layer on at least a portion of the lead.

* * * * *